US005750455A

United States Patent [19]
Chauvin et al.

[11] Patent Number: 5,750,455
[45] Date of Patent: *May 12, 1998

[54] CATALYTIC COMPOSITION AND PROCESS FOR THE ALKYLATION OF ALIPHATIC HYDROCARBONS

[75] Inventors: Yves Chauvin, Le Peco; André Hirschauer, Montesson; Hélène Olivier, Rueil Malmaison, all of France

[73] Assignee: Institut Francais Du Petrole, Rueil Malmaison, France

[*] Notice: The term of this patent shall not extend beyond the expiration date of Pat. No. 5,693,585.

[21] Appl. No.: 547,205

[22] Filed: Oct. 24, 1995

[30] Foreign Application Priority Data

Oct. 24, 1994 [FR] France ................... 94 12778

[51] Int. Cl.[6] .................. B01J 31/00; B01J 27/122; B01J 23/70; C07C 2/58
[52] U.S. Cl. .................. 502/164; 502/165; 502/167; 502/169; 502/225; 502/345; 502/346; 502/355; 585/727; 585/728
[58] Field of Search .................. 502/164, 165, 502/167, 169, 225, 345, 346, 355; 585/727, 728

[56] References Cited

U.S. PATENT DOCUMENTS

| | | | |
|---|---|---|---|
| 2,337,014 | 12/1943 | Crawford | 585/728 |
| 4,922,049 | 5/1990 | Byers | 585/327 |
| 4,940,831 | 7/1990 | Drake et al. | 585/836 |
| 5,406,018 | 4/1995 | Sherman | 585/729 |

FOREIGN PATENT DOCUMENTS

| | | | |
|---|---|---|---|
| 0 488 073 | 6/1992 | European Pat. Off. | B01J 31/14 |
| 0 553 009 | 7/1993 | European Pat. Off. | B10J 31/02 |
| 0 576 323 | 12/1993 | France | C07C 2/60 |
| WO 91/16283 | 10/1991 | WIPO | C07C 2/68 |

*Primary Examiner*—Glenn Caldarola
*Assistant Examiner*—Patricia L. Hailey
*Attorney, Agent, or Firm*—Millen, White, Zelano, & Branigan, P.C.

[57] ABSTRACT

The invention concerns a catalytic composition resulting from mixing at least one aluminum halide, at least one quaternary ammonium halide and/or at least one amine halohydrate and at least one cuprous compound, preferable a halide. The invention also concerns a process for the alkylation of isoparaffins by olefins with that composition.

21 Claims, No Drawings

CATALYTIC COMPOSITION AND PROCESS FOR THE ALKYLATION OF ALIPHATIC HYDROCARBONS

The present invention concerns an ionic catalytic composition which is at least in part liquid and a process using that composition for the production of paraffinic hydrocarbons by the addition reaction of olefins on isoparaffins in the presence of modified catalysts of Friedel-Craft type.

A large number of liquid or solid acid catalysts are known which are capable of effecting alkylation of isoparaffins such as isobutane or isopentane by olefins such as propylene, but-1- and -2-enes and isobutene. The catalysts which are most widely used in industrial practice are concentrated sulphuric acid and hydrofluoric acid alone or mixed with Lewis acids such as boron trifluoride. Those processes suffer from major disadvantages: hydrofluoric acid by virtue of its toxicity and its high degree of volatility; and sulphuric acid by virtue of a substantial level of consumption of the catalyst requiring burdensome re-treatment. That is the reason for recommending the use of catalysts which are solid or which are supported on solids such as aluminosilicates or metal oxides such as zirconia treated with sulphuric acid. However solid catalysts are generally found to present a low level of selectivity and a low degree of activity. The use of aluminium chloride has also been studied and proposed.

French patents Nos 2 626 572 and 2 692 888 proposed catalysing the paraffinic alkylation reaction by using liquid ionic complexes that are made by aluminium halides with some quaternary ammonium halides or with some amine halohydrates. Those complexes which are also referred to as "molten salts" are described by C. H. Hussey in "Advances in Molten Salts Chemistry", volume 5, page 185, Elsevier, New York, 1985 and by C. A. Angell and J. W. Shuppert in J. Phys. Chem. 84, 538, 1980. Those catalysts are particularly simple to use.

It has been shown in those patents that the most active catalysts are obtained by mixing an equivalent of quaternary ammonium halide or amine halohydrate with an equivalent and more of aluminium trihalide.

It has now been found that the addition of compounds of copper (I) and in particular cuprous halides to the foregoing salts improved the selectivity and stability of the catalyst, made it possible to avoid the introduction of additional protons for reactivating the catalyst and reduced the chlorine content of the alkylates which are the reaction products.

More precisely the subject of the invention is a catalytic composition comprising at least one aluminium halide, at least one quaternary ammonium halide and/or at least one amine halohydrate and at least one cuprous compound. Another subject of the invention is a process for the alkylation of at least one isoparaffin by at least one olefin, in which process the paraffins and the olefins are brought into contact with said catalytic composition.

The aluminium halides which can be used in accordance with the invention are preferably aluminium chloride and aluminium bromide. The recommendation is against hydrocarbylaluminium halides.

The quaternary ammonium halides which can be used in accordance with the invention are those described in French patent No 2 626 572. The quaternary ammonium salts which are acyclic or form part of a cycle respond to the following general formulae:

$$R^1R^2R^3R^4N^+ \quad X^- \tag{I}$$

$$R^1R^2N^+=CR^3R^{4+}X^- \tag{II}$$

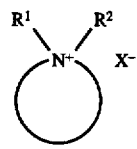
(III)

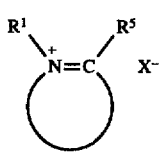
(IV)

in which $R^1$, $R^2$, $R^3$, $R^4$ or $R^5$ which are identical or different each represent hydrocarbyl residues generally comprising from 1 to 12 carbon atoms, for example alkyl, cycloalkyl, aryl and aralkyl, while $R^5$ may also be hydrogen or substituted hydrocarbyl residues comprising for example other atoms such as nitrogen. $R^1$, $R^2$, $R^3$ or $R^4$ may also be hydrogen, except for the cation NH4+ and preferably a single substituent ($R^1$, $R^2$, $R^3$, $R^4$ or $R^5$) may represent hydrogen. Radicals such as $R^6$ may unite two molecules such as above, such as for example $R^1R^2N^+=CR^3-R^6-CR^3=N^+R^1R^2(X^-)_2$, while $R^6$ may be an alkylene or again phenylene residue, with the radicals $R^1$, $R^2$ and $R^3$ being defined as above.

The rings III and IV are formed by from 4 to 10 atoms, preferably 5 to 6 atoms which, besides nitrogen of quaternary ammonium, may comprise carbon atoms or possibly other nitrogen atoms, generally 1 or 2.

Among the groups $R^1$, $R^2$, $R^3$, $R^4$ or $R^5$ mention will be made of methyl, ethyl, propyl, isopropyl, butyl, secondary butyl, tertiary butyl, amyl, methylene, ethylidene, phenyl or benzyl radicals; $R^6$ may be a methylene, ethylene, propylene or phenylene group.

In those formulae X represents a halide ion, for example the bromide ion or the chloride ion.

By way of examples of ammonium salts which can be used in accordance with the invention, mention may be made more particularly of salts of imidazolium or pyridinium such as N-butylpyridinium chloride, ethylpyridinium bromide, 3-butyl 1-methyl imidazolium chloride, diethylpyrazolium chloride and 3-ethyl 1-methyl imidazolium chloride.

The amine halohydrates and in particular chlorohydrates or the amine bromohydrates which can be more particularly used in accordance with the invention preferably comprise one mole of halohydric acid (chlorohydric or bromohydric preferred) per mole of amine but they may also comprise two moles of acid per mole of amine. It is also possible to use mixtures of halohydrates with one mole and with two moles of halohydric acid. The halohydrates derive from acyclic amines or diamines or amines forming part of a ring which may comprise one or more nitrogen atoms and which correspond to the following general formulae:

$$NR^{'1}R^{'2}R^{'3} \tag{I}$$

$$R^{'1}N=CR^{'2}R^{'3} \tag{II}$$

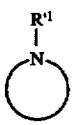
(III)

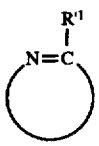

(IV)

in which $R'^1$, $R'^2$ and $R'^3$ which are identical or different represent hydrocarbyl residues generally comprising from 1 to 12 carbon atoms, for example alkyl, cycloalkyl, aryl and aralkyl. One of those substituents $R'^1$, $R'^2$ and $R'^3$ may be hydrogen. The rings III and IV are generally formed by from 4 to 10 atoms, preferably 5 to 6 atoms which, besides a nitrogen atom or atoms, may comprise carbon atoms which are joined by single or double bonds. The rings III and IV may be condensed with other rings and carry substituents as defined above, amine functions and atoms of fluorine, chlorine and bromine.

Among the groups $R'^1$, $R'^2$ and $R'^3$ mention will be made of the methyl, ethyl, propyl, isopropyl, butyl, sec-butyl, amyl, methylene, ethylene, phenyl and benzyl radicals. The rings such as IV are represented by the families of pyridines, imidazoles, triazines, pyrazoles, pyrimidines and triazoles.

The preferred halohydrates are chlorohydrates or bromohydrates of pyridine, 2-, 3- or 4- picolines, lutidines, 2-ethyl pyridine, 3-isopropyl pyridine, 3-isopropyl pyridine, 2- or 4-chloropyridine, N,N-dimethyl-4-aminopyridine, N-methylimidazole, N-butylimidazole, piperidine and N-methylimidazoline.

A crucial essential agent according to the invention is the presence of copper (I). The compounds of copper (I) which can be used in accordance with the invention are for example acetate, sulphate, nitrate, perchlorate and the compound $C_u^+AlCl_4^-$. Very advantageously, it is a halide, which avoids the introduction of supplementary ions into the reaction medium.

The copper halides which are preferred in accordance with the invention are cuprous chloride and cuprous bromide.

A cupric compound may also be introduced as the starting product, but it is transformed in the reaction medium, at least in part, into a cuprous compound.

The components of the mixtures as defined above are preferably used in molar ratios of aluminium halide:quaternary ammonium halide and/or amine halohydrate of between 1:1.1 and 1:3.5, preferably between 1:2 and 1:3; and aluminium halide:cuprous halide of between 1:0.1 and 1:1, preferably between 1:0.2 and 1:0.5.

The compounds which are involved in the composition according to the invention may be mixed in any order at a temperature between −20° C. and +80° C. Mixing may be effected by simply bringing the compounds into contact followed by agitation until a handlable suspension or a liquid is formed. The mixing operation can be effected outside of the alkylation reactor or in that reactor, with or without hydrocarbons. The mixing operation can advantageously be effected in the presence of an organic polar liquid compound which is of low basicity and which is sufficiently volatile and which is miscible with the mixture of the components of the mixture and which will then be removed by evaporation prior to the alkylation reaction. The compounds which can be used in accordance with the invention are for example ethers and nitriles and among the latter more particularly acetonitrile or propionitrile. In that way there is produced a homogenous preparation (and no longer a suspension) which can be easily handled.

The invention also concerns a catalytic composition with the mixture of components as defined above, which also includes at least one organic compound, a solvent for the mixture of the components, as is defined above.

The invention also concerns a process for the alkylation of at least one isoparaffin by at least one olefin in the presence of a catalytic composition as defined above.

The paraffins which can be alkylated in accordance with the invention are more particularly isobutane, isopentane, 2-methylbutane, and 2-methyl and 3-methylpentanes. The olefins which can be used in accordance with the invention are more particularly ethylene, propylene, n-butenes, isobutene, n-pentenes and iso-pentenes and more generally olefins having from 2 to 7 carbon atoms. The invention is also advantageous for treating a $C_6$ effluent resulting from the dimerisation of an olefinic $C_3$ cut.

The catalytic alkylation reaction is effected in a liquid hydrocarbon phase in a closed system, in a semi-open system or continuously, with a reaction stage, which is the current practice in regard to aliphatic alkylation. The isoparaffin and the olefin may be introduced separately or as a mixture. In a continuous or semi-continuous sytem the molar ratio between the isoparaffin and the olefin is for example between 2 and 100 and advantageously between 10 and 50, preferably between 5 and 20. In a semi-open system, the procedure will involve firstly introducing isoparaffin and then olefin, or a mixture of isoparaffin and olefin. Vigorous agitation should ensure good contact between the reactants and the catalytic mixture. The reaction temperature may be between −40° C. and +70° C., preferably between −20° C. and +30° C. The pressure may be between atmospheric pressure and 10 MPa but it will be sufficient to keep the reactants in the liquid phase. The heat generated by the reaction may be removed by any means known to the man skilled in the art. On issuing from the reactor the hydrocarbon phase is separated from the ionic phase by settlement, then the hydrocarbons are separated by distillation and the initial isoparaffin which has not been converted is recycled to the reactor.

It has been observed that, when the catalyst has lost a marked part of its activity, it can be re-activated by adding at least one electrophile additive, for example an aluminium halide, a halohydric acid or an alkyl halide.

The amounts of additive added are preferably such that the aluminium halide:additive molar ratio is between 0.001 and 1 and advantageously between 0.001 and 0.1.

The following Examples illustrate the invention without limiting the scope thereof.

EXAMPLE No 1

Preparation of organochloroaluminate

Using a glass balloon flask provided with a magnetic agitator and which has been purged of air and moisture and which is maintained at 10° C., 22.9 g of freshly distilled aluminium chloride, 20 mL of heptane and, in portions, 16.2 g of 1-butyl 3-methyl imidazolium chloride are successively introduced. A liquid composition is thus obtained.

Alkylation of the isobutane by but-2-ene 7 mL (9.5 g) of the foregoing composition are introduced into a glass reactor intended for the alkylation reaction in which 1.9 g of anhydrous cuprous chloride is added. That gives a viscous suspension which can nonetheless be vigorously agitated by means of a magnetic stirrer rod. 40 g of isobutane and 8.3 g of butane are introduced into that suspension (internal standard). An isobutane/n-butane/but-2-ene mixture containing 40% by weight of butene is then continuously injected at a rate of 0.3 volume of liquid but-2-ene per volume of catalytic composition and per hour (V/V/H=0.3). The reaction is stopped when the conversion of the isobutane is from 15 to 30% according to the tests (that is to say from 5 to 10 reaction hours). The hydrocarbon phase is taken off and the procedure begins again as before. The reaction is re-done 16 times in succession. Analysis of the mixture of hydrocarbons is effected by vapour phase chromatography. Conversion of the but-2-ene was always quantitative. The mean composition of the alkylate, the calculated values of the "Research" and "Engine" octane numbers and the content of organic chlorine are given in Table 1.

COMPARATIVE EXAMPLE (without cuprous halide)

Operation was effected under conditions identical to those of Example 1 but in the absence of cuprous chloride. After five successive tests it was found that the conversion of but-2-ene was no longer total and that the selectivity in relation to compounds with a high octane number decreased. The mean composition of the alkylate, the calculated values of the "Research" and "Engine" octane numbers and the content of organic chlorine are given in Table 1.

EXAMPLE No 2
Preparation of the catalytic composition

Using a glass balloon flask provided with a magnetic agitator and purged of air and moisture and maintained at 10° C., 22.9 g of freshly distilled aluminium chloride, 20 mL of heptane and, in portions, 16.2 g of 1-butyl 3-methyl imidazolium chloride are successively introduced. That gives a liquid composition which is introduced into another balloon flask containing 7.5 g of anhydrous cuprous chloride. Added to the resulting suspension is 20 mL of dry acetonitrile, that resulting in a homogenous liquid. The acetonitrile is evaporated. The mixture then becomes viscous. Added thereto is 9 mL of a chloroaluminate which is identical to that which was used for the preceding preparation. That gives a homogenous liquid which was used for the alkylation operation.

Alkylation of the isobutane by but-2-ene

Operation is as in Example 1. The results obtained are comparable: RON (calculated): 98.2; EON (calculated): 96.1.

TABLE 1

| | (% by weight) | | |
|---|---|---|---|
| | Example 1 | | Comparative example |
| | Average | 1st drawing | Average |
| 2-Me butane | 3 | 10.4 | 8.6 |
| Di 2,3-Me butane | 2.6 | 4 | 5.1 |
| C$_6$ (others) and C$_7$ | 2.9 | 7.1 | 6 |
| Total light H.C.s | 8.5 | 21.3 | 19.7 |
| Tri 2,2,4-Me pentane | 50.1 | 35.7 | 29.5 |
| Tri 2,2,3-Me pentane | 2.2 | 7 | 5.1 |
| Tri 2,3,4-Me pentane | 12.8 | 4.7 | 7.6 |
| Tri 2,3,3-Me pentane | 15.4 | 9.7 | 9.5 |
| Total tri Me-pentanes | 80.5 | 57.1 | 51.7 |
| Di 2,5-Me hexane | 1.2 | 3.8 | 1.1 |
| Di 2,4-Me hexane | 1.4 | 4.6 | 2.2 |
| Di 2,3-Me hexane | 1.4 | 2.3 | 1.2 |
| Total di Me-hexanes | 4 | 10.7 | 4.5 |
| Tri 2,2,5-Me hexane | 2.4 | 4.5 | 7 |
| C$_{9(and+)}$ (others) | 3.8 | 5.5 | 15.7 |
| C$_{12+}$ | 0.7 | 0.4 | 1.3 |

TABLE 1-continued

| | (% by weight) | | |
|---|---|---|---|
| | Example 1 | | Comparative example |
| | Average | 1st drawing | Average |
| Total heavy H.C.s | 6.9 | 10.4 | 24 |
| RON (calculated) | 98 | 93 | 93.9 |
| EON (calculated) | 96 | 91 | 91.6 |
| Chlorine (ppm) | 40 | 40 | 85 |

We claim:

1. A catalytic composition suitable for alkylation comprising at least one aluminium halide, at least one quaternary ammonium halide and/or at least one amine halohydrate, and at least one cuprous compound.

2. A catalytic composition according to claim 1 characterised in that the cuprous compound is a cuprous halide.

3. A catalytic composition according to claim 1 wherein the cuprous compound is selected from the group consisting of cuprous acetate, sulphate, perchlorate, nitrate, Cu$^+$AlCl$_4^-$, copper I chloride and copper I bromide.

4. A catalytic composition according to claim 1 wherein the aluminium halide is selected from the group consisting of aluminium chloride and aluminium bromide.

5. A catalytic composition according to claim 1 comprising a quaternary ammonium halide selected from the group consisting of compounds of the general formulae:

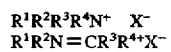

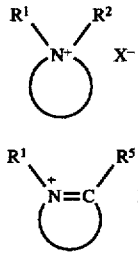

in which R$^1$, R$^2$, R$^3$, R$^4$ and R$^5$ which are identical or different represent hydrocarbyl residues having from 1 to 12 carbon atoms, wherein R$^5$ may also be hydrogen, and in which the rings are formed by from 4 to 10 atoms, X representing the halide ion.

6. A catalytic composition according to claim 1 comprising a quaternary ammonium halide selected from the group consisting of compounds of the general formulae:

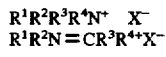

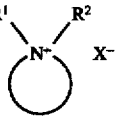

-continued

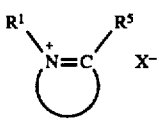

in which $R^1$, $R^2$, $R^3$, $R^4$ and $R^5$ represent hydrogen, except for $NH_4+$.

7. A catalytic composition according to claim 1 comprising a quaternary ammonium halide of the following general formula:

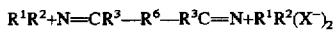

in which $R^1$, $R^2$ and $R^3$ which are identical or different represent hydrocarbyl residues having from 1 to 12 carbon atoms and $R^6$ represents an alkylene or phenylene residue, X representing the halide ion.

8. A catalytic composition according to claim 1 comprising a quaternary ammonium halide is of the following general formula:

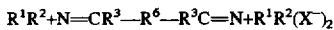

in which $R^1$, $R^2$ and $R^3$ represent hydrogen.

9. A catalytic composition according to claim 1 comprising a quaternary ammonium halide selected from the group consisting of N-butylpyridinium chloride, ethylpyridinium bromide, 3-butyl 1-methyl imidazolium chloride, diethylpyrazolium chloride and 3-ethyl 1-methyl imidazolium chloride.

10. A catalytic composition according to claim 1 comprising an amine halohydrate selected from the group consisting of halohydrates comprising one mole of halohydric acid per mole of amine and halohydrates comprising 2 moles of halohydric per mole of amine.

11. A catalytic composition according to claim 1 comprising an amine halohydrate derived from an amine selected from the group of compounds of the following general formulae:

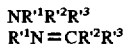

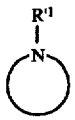

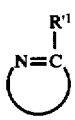

in which $R'^1$ $R'^2$ and $R'^3$ which are identical or different represent hydrocarbyl residues having from 1 to 12 carbon atoms and in which the rings are formed by from 4 to 10 atoms, wherein one of the substituents $R'^1$, $R'^2$ and $R'^3$ may be hydrogen.

12. A catalytic composition according to claim 1 comprising halohydrates selected from the group consisting of chlorohydrates and bromohydrates of pyridine, 2-, 3- and 4-picolines, N-methylimidazole, N-butylimidazole, lutidines, 2-ethyl pyridine, 3-isopropyl pyridine, 2- or 4-chloropyridine, N,N-dimethyl-4-amino pyridine, piperidine and N-methylimidazoline.

13. A catalytic composition according to claim 1 wherein the molar ratio between the aluminium halide and the quaternary ammonium halide and/or the amine halohydrate is between 1:1.1 and 1:3.5.

14. A catalytic composition according to claim 1 wherein the molar ratio between the aluminium halide and the cuprous halide is between 1:0.1 and 1:1.

15. A catalytic composition according to claim 1 also comprising at least one organic polar liquid compound of low basicity which is miscible with the mixture of the components.

16. A catalytic composition according to claim 1 also comprising at least one electrophile additive.

17. A catalytic composition according to claim 16 wherein the aluminium halide:additive molar ratio is between 0.001 and 1.

18. A catalytic composition according to claim 1 also comprising at least one additive selected from the group formed by an aluminium halide, a halohydric acid and an alkyl halide.

19. A process for the alkylation of at least one isoparaffin by at least one olefin in the presence of a catalytic composition according to claim 1.

20. A process for the preparation of a catalytic composition according to claim 1 wherein at least one aluminium halide, at least one quaternary ammonium halide and/or at least one amine halohydrate and at least one cuprous compound are brought into contact at a temperature of between $-20°$ C. and $+80°$ C. in the presence of an organic polar liquid compound which is of low basicity and which is miscible with the mixture of the components.

21. A catalytic composition consisting essentially of at least one aluminium halide, at least one quaternary ammonium halide and/or at least one amine halohydrate, and at least one cuprous compound.

* * * * *